United States Patent [19]
Schamper et al.

[11] Patent Number: 5,989,531
[45] Date of Patent: Nov. 23, 1999

[54] ANTIPERSPIRANT FORMULATION FOR POROUS APPLICATOR

[75] Inventors: Thomas Schamper, Cranbury; Bhalchandra Moghe, White House Station; Morton L. Barr, East Brunswick; Ching-Min Kimmy Wu, Kendall Park, all of N.J.

[73] Assignee: Colgate-Palmolive Company, New York, N.Y.

[21] Appl. No.: 09/191,897

[22] Filed: Nov. 13, 1998

[51] Int. Cl.⁶ .............................. A61K 7/32; A61K 7/34; A61K 7/38; A61K 7/00
[52] U.S. Cl. .................. 424/65; 424/66; 424/68; 424/401
[58] Field of Search ................. 424/401, 65, 66, 424/68

[56] References Cited

U.S. PATENT DOCUMENTS

| | | |
|---|---|---|
| 4,268,499 | 5/1981 | Keil ........................................ 424/68 |
| 4,322,400 | 3/1982 | Yuhas . |
| 4,673,570 | 6/1987 | Soldati . |
| 4,853,214 | 8/1989 | Orr . |
| 4,937,069 | 6/1990 | Shin . |
| 5,008,103 | 4/1991 | Raleigh et al. . |
| 5,019,375 | 5/1991 | Tanner et al. . |
| 5,069,897 | 12/1991 | Orr . |
| 5,102,656 | 4/1992 | Kasat . |
| 5,120,531 | 6/1992 | Wells et al. . |
| 5,175,325 | 12/1992 | Brown et al. . |
| 5,216,033 | 6/1993 | Pereira et al. ............................. 514/63 |
| 5,225,188 | 7/1993 | Abrutyn et al. . |
| 5,243,010 | 9/1993 | Choi et al. . |
| 5,272,241 | 12/1993 | Lucarelli et al. . |
| 5,384,117 | 1/1995 | Vu et al. . |
| 5,500,209 | 3/1996 | Ross et al. . |
| 5,523,375 | 6/1996 | Raleigh et al. . |
| 5,567,073 | 10/1996 | Laforcade et al. ....................... 401/190 |
| 5,575,990 | 11/1996 | Benfatto .................................... 424/65 |
| 5,871,717 | 2/1999 | Bretzler et al. . |
| 5,882,637 | 3/1999 | Putnam . |

FOREIGN PATENT DOCUMENTS

| | | |
|---|---|---|
| 0291334 | 5/1988 | European Pat. Off. . |
| WO9205767 | 4/1992 | WIPO . |
| WO9800097 | 1/1998 | WIPO . |
| WO9800105 | 1/1998 | WIPO . |

*Primary Examiner*—Shelley A. Dodson
*Assistant Examiner*—Marina Lamm
*Attorney, Agent, or Firm*—Rosemary M. Miano

[57] ABSTRACT

The invention comprises a liquid composition which provides a drier feel and reduced leakage when used with certain types of applicators, especially an applicator having a porous surface, which composition is made by combining an active phase and a silicone phase. The active phase is made by combining: (a) 10–70% of a selected glycol; (b) 0.1–10% of a nonionic emulsifier having an HLB greater than 8; (c) 0.01–30% of a cosmetically active ingredient; and (d) 0–20% of ethanol and/or isopropanol. The silicone phase is made by combining: (a) from 0.1–10% of a selected emulsifier; (b) 0–30% of a non-volatile silicone; (c) 0–30% of a volatile silicone; and (d) 0–25% of an organic emollient; provided that: (a) the silicone phase contains at least 10% silicone; (b) the ratio of silicone phase to active phase is in the range of 1:1 to 1:4; and (c) the composition is processed to maintain a viscosity in the range of 2,000–200,000 centipoise ("cps").

18 Claims, No Drawings

ANTIPERSPIRANT FORMULATION FOR POROUS APPLICATOR

FIELD OF THE INVENTION

This invention relates to antiperspirant and/or deodorant formulations which provide an improved feel (such as a drier feel) to the underarm area when used in combination with selected types of applicators, especially porous applicators. Examples of such applicators are found in European patent application number 0 732 273 B1; PCT case WO 98/12122; PCT case WO 98/04236; U.S. patent application filed on Oct. 7, 1998, as attorney docket number IR 6020 (Serial Number not yet accorded); U.S. patent application filed on Nov. 4, 1998, as attorney docket number IR 6020-01 (Serial Number not yet accorded) and owned by the same entity as this application. An example of an applicator device which has a dispenser head made of a porous material placed over a pressurized reservoir equipped with a dispensing valve is found in U.S. Pat. No. 5,567,073 to De Laforcade et al.

BACKGROUND OF THE INVENTION

A large variety of antiperspirant and/or deodorant formulations have been described in the patent literature and/or have been made commercially available. These products have included solids (for example, wax and gel sticks), semi-solids (for example, gels and creams), liquids (for example, roll-on products) and sprays (both aerosol and non-aerosol). In recent years a strong emphasis has been placed on improving both the performance and the aesthetics of these products. Any improvements must take into account both the form of the composition and the method of application.

With regard to emulsions, U.S. Pat. No. 4,673,570 to Soldati describes uniform, clear gelled antiperspirant compositions, free of waxes wherein the emulsions comprise in combination a volatile silicone fluid, a silicone emulsifier (such as a mixture of cyclomethicone and dimethicone copolyol), a destabilizing auxiliary emulsifier, water, a non-volatile emollient (such as C10–C20 alkyl fatty esters and ethers), linear silicone fluids, a coupling agent (such as low molecular weight alcohols and glycols), an active antiperspirant component and other ancillary agents.

U.S. Pat. No. 5,008,103 to Raleigh et al describes water-in-oil antiperspirant emulsions having a discontinuous polar phase containing water and optionally containing an emulsifier with a hydrophilic-lipophilic balance (HLB value) greater than 8, and a volatile silicone continuous phase with a dimethicone copolyol emulsifier. The HLB parameter is a well known parameter the calculation of which is disclosed and explained in numerous references. For nonionic surfactants, data obtained by actual analysis is usually a more accurate measure of HLB values (rather than theoretical determinations). For purposes of this invention it is intended that either the actual or theoretical HLB value may be used as the basis for selection. U.S. Pat. No. 5,401,870 to Raleigh et al and U.S. Pat. No. 5,292,503 to Pereira et al describe similar subject matter.

U.S. Pat. No. 5,216,033 to Pereira et al describes a transparent water-in-oil emulsion containing a silicone phase with a dimethicone copolyol and an aqueous phase containing a refractive index "transparency structurant" to produce a refractive index matched clear emulsion. The transparency structurant is a C3–C8 polyhydric alcohol.

There remained a problem with tack (stickiness), however, and attempts to create better products included removing water from the formulations. A presentation entitled "Novel Formulations Based on Nonaqueous Emulsions of Polyols in Silicones", by A. Zombeck and G. Dahms (Paper presented at the $19^{th}$ IFSCC Congress, Sydney, Australia, Oct. 22–25, 1996) describes stable anhydrous antiperspirant emulsions prepared with propylene glycol; however, clear emulsions are not reported. Other parties have added ethanol but the quantities are so large that the regular emulsion (macroemulsion) is converted into a microemulsion with the result that the formulations are tacky.

U.S. Pat. No. 5,599,533 to Stepniewski et al describes the use of silicone elastomer in an aqueous water-in-oil emulsion, but does not describe a clear emulsion.

EP 0 732 273 B1 to De Laforcade describes an applicator and a viscous product for such applicator. These products are creamy or pasty or in the form of a foam. The applicator has a porous, rigid applicator element. A dome structure is used for the dispensing surface and may be made of sintered material having pores in the range of 1–500 microns which communicate with one another in all directions.

Other examples of applicators useful with gel compositions which applicators have a plurality of surfaces include U.S. Pat. Nos. 4,801,052 and 5,372,285 as exemplified in Speed Stick® and Right Guard® gel products. Yet another applicator for semisolid products utilizes a sintered plastic material called Porex that has random, nonlinear, branched pores of varying cross-sectional diameters. Pressure relief mechanisms to solve post-extrusion of product and avoid leakage of unwanted product are described in U.S. Pat. Nos. 5,540,361 and 5,547,302. U.S. Pat. No. 5,547,302 also describes the use of a thin, flexible mesh with a plurality of discrete openings extending through the mesh as an applicator surface.

In a different approach, the use of an improved applicator with porous structures has been developed. This is the subject of the co-pending cases assigned to the same assignee as this application. This applicator requires a new type of formulation for a satisfactory product, in particular forming a product that minimizes leaking problems and has superior aesthetics when applied to the underarm. Previous formulations, especially including certain gels and other compositions containing thickening agents are not suitable because they do not have the desired aesthetics. On the other hand, one must be sensitive to the use of liquids in these new applicators since the liquid can ooze or drop out of the container. Separation of phases must also be prevented. Thus, there remains a need for new compositions which are suitable for use with porous top applicators which have mini-holes, pores, screen or woven applicator surfaces.

It is, therefore, an object of the present invention to provide antiperspirant and/or deodorant compositions which are suitable for use with the applicators described above. It is a further object of the invention to provide compositions suitable for use with the applicators described above which minimize problems from leaking. It is yet another object of the invention to provide formulations suitable for use with the applicators described above which minimize problems of phase separation. It is an additional object to provide formulations suitable for use with the applicators described above which are easy and convenient for the consumer to use. These and other objects will become apparent from the following description of the invention.

SUMMARY OF THE INVENTION

The invention comprises a liquid composition which provides a drier feel and reduced leakage when used with certain types of applicators, especially an applicator having a porous surface, which composition is made by combining an active phase and a silicone phase.

The active phase is made by combining:
(a) 10–70% of a glycol selected from the group consisting of propylene glycol, dipropylene glycol, tripropylene glycol, 2-methyl-1,3-propanediol, low molecular weight polyethylene glycol, and mixtures of any of the foregoing;
(b) 0.1–10% of a nonionic emulsifier having an HLB greater than 8;
(c) 0.01–30% (on an anhydrous solids basis) of a cosmetically active ingredient selected from the group consisting of antiperspirant actives and deodorant actives which cosmetically active ingredient is in the form of a powder or a solution; and
(d) 0–20% (for example, 5–20%) of an alcohol selected from the group consisting of ethanol and isopropanol, aqueous solutions thereof and mixtures thereof (especially ethanol, for example either as anhydrous or 95%).

The silicone phase is made by combining:
(a) from 0.1–10% of an emulsifier selected from the group consisting of
  (i) dimethicone copolyols having an HLB less than 7;
  (ii) nonionic emulsifiers having an HLB value less than 7; and
  (iii) mixtures of (i) and (ii);
(b) 0–30% of a non-volatile silicone,
(c) 0–30% of a volatile silicone; and
(d) 0–25% of an organic emollient; provided that:
(a) the silicone phase contains at least 10% silicone;
(b) that the ratio of silicone phase to active phase is in the range of 1:1 to 1:4; and
(c) the composition is processed to maintain a viscosity in the range of 2,000–200,000 centipoise ("cps").

Optionally, one or more of each of fragrance, color, preservative can be added to the appropriate phase as is known to those skilled in the art.

DETAILED DESCRIPTION OF THE INVENTION

For the active phase the high HLB (greater than 8, particularly in the range of 8–12) nonionic emulsifier (or mixtures thereof) used in this invention (each of which can also be a mixture or blend of surfactants) include, but are not limited to at least one member selected from the group consisting of:
(a) sorbitan esters and ethoxylated sorbitan esters (for example, PEG-20 sorbitan isostearate, sorbitan monolaurate, polysorbate-20, polysorbate-40, polysorbate-60, polysorbate-80);
(b) ethoxylates (for example, Ceteth-20, PEG-30 castor oil, PEG-40 hydrogenated castor oil, PEG-60 hydrogenated castor oil, Laureth-7, Isolaureth-6, Steareth-10, Steareth-20, Steareth-21, Steareth-100, Ceteareth-12, Oleth-5, Oleth-10);
(c) PEG esters (for example, PEG-8 oleate, PEG-8 laurate, PEG-8 dilaurate, PEG-12 dilaurate, PEG-80 diisostearate, PEG-25 stearate, PEG-40 stearate, and PEG-100 stearate);
(d) propoxylates (for example, PPG-2-ceteareth-9, and PPG-5-ceteth-20);
(e) ethoxylated modified triglycerides (for example, PEG-20 corn glycerides, PEG-12 palm kernel glycerides);
(f) alkylphenol aromatic ethoxylates (for example, octoxynol-20 and nonoxynol-40);
(g) block copolymers which are alkoxylated glycols having ethoxylated and propoxylated segments (for example, Poloxamers 124 and 234); and
(h) silicone polyethers (for example, dimethicone copolyols (SILWET L-7200 and L-7657)).

These non-ionic emulsifiers are further selected to be acceptable in terms of color, odor and safety.

The active phase surfactant or blend of surfactants incorporated into the compositions of the present invention can, illustratively, be included in amounts of 0.1–10%, preferably 0.1–5%, and more preferably 0.2–2% by weight based on the total weight of the composition.

For the antiperspirant active used in the active phase various antiperspirant active materials that can be utilized according to the present invention provided that they are soluble at a suitable concentration in the active phase. These include conventional aluminum and aluminum/zirconium salts, as well as aluminum/zirconium salts complexed with a neutral amino acid such as glycine, as known in the art. See each of European Patent Application Number. 512,770 A1 and PCT case WO 92/19221, the contents of each of which are incorporated herein by reference in their entirety, for disclosure of antiperspirant active materials. The antiperspirant active materials disclosed therein, including the acidic antiperspirant materials, can be incorporated in the compositions of the present invention if they are soluble in the active phase. Suitable materials include (but are not limited to) aluminum chlorides (various types including, for example, anhydrous form, hydrated form, etc.), zirconyl hydroxychlorides, zirconyl oxychlorides, basic aluminum chlorides, basic aluminum chlorides combined with zirconyl oxychlorides and hydroxychlorides, and organic complexes of each of basic aluminum chlorides with or without zirconyl oxychlorides and hydroxychlorides and mixtures of any of the foregoing. These include, by way of example (and not of a limiting nature), aluminum chlorohydrate, aluminum chloride, aluminum sesquichlorohydrate, aluminum chlorohydrol-propylene glycol complex, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum dichlorohydrate, aluminum chlorohydrex PG, aluminum chlorohydrex PEG, aluminum dichlorohydrex PG, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as tin or titanium salts used alone or in combination with aluminum compounds (for example, aluminum-stannous chlorohydrates), aluminum nitratohydrate and its combination with zirconyl hydroxychlorides and nitrates, can be incorporated as an antiperspirant active ingredient in antiperspirant compositions according to the present invention. Preferred antiperspirant actives that can be incorporated in the compositions of the present invention include the enhanced efficacy aluminum salts and the enhanced efficacy aluminum/zirconium salt-glycine materials, having enhanced efficacy due to improved molecular distribution, known in the art and discussed, for example, in PCT No. WO92/19221, the contents of which are incorporated by reference in their entirety herein.

Antiperspirant actives can be incorporated into compositions according to the present invention in amounts in the range of 0.1–30% (on an anhydrous solids basis), preferably 5–25%, by weight, of the total weight of the composition. The amount used will depend on the formulation of the composition. For example, at amounts in the lower end of the broader range (for example, 0.1–5%), the antiperspirant active material will not substantially reduce the flow of perspiration, but will reduce malodor, for example, by acting as a deodorant material.

Deodorant active materials can be selected from several types of materials:

(a) lesser amounts of antiperspirant actives, such as in the range of 0.1–5.0 percent by weight based on the total weight of the composition;

(b) fragrances, such as in the range of 0.5–3.0 percent by weight based on the total weight of the composition;

(c) effective amounts of antimicrobial agents, for example, 0.01–1.0 percent by weight based on the total weight of the composition; examples include bacteriostatic quaternary ammonium compounds (such as cetyl trimethyl-ammonium bromide, and cetyl pyridinium chloride), 2, 4, 4'-trichloro-2'-hydroxydiphenylether (Triclosan), N-(4-chlorophenyl)-N'-(3,4-dichlorophenyl)urea (Triclocarban), silver halides, octoxyglycerin (SENSIVA™ SC 50) and various zinc salts (for example, zinc ricinoleate). Triclosan or Triclocarban can, illustratively, be included in an amount of from 0.05% to about 0.5% by weight, of the total weight of the composition.

Optionally, in the active phase additional ingredients can be included such as one or more of the following:

(a) up to 10% added water (for example, 5–10%) can be included, which can include any water that comes in with the ingredients (for example, alcohol/water mixtures) or in the waters of hydration of the antiperspirant active as well as water added separately; and (b) from 0.1–5% of fragrance, color, preservatives, antimicrobial agents.

For the silicone phase, the dimethicone copolyols that can be used are of the type described in the art provided that they are selected to have an HLB value less than 7. These include copolyols of the following Formulae I and II. Formula I materials may be represented by:

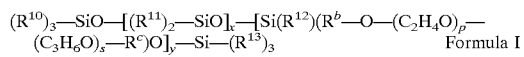

$(R^{10})_3$—SiO—[$(R^{11})_2$—SiO]$_x$—[Si($R^{12}$)($R^b$—O—$(C_2H_4O)_p$—$(C_3H_6O)_s$—$R^c$)O]$_y$—Si—$(R^{13})_3$    Formula I wherein each of $R^{10}$, $R^{11}$, $R^{12}$ and $R^{13}$ may be the same or different and each is selected from the group consisting of C1–C6 alkyl; $R^b$ is the radical —$C_mH_{2m}$—; $R^c$ is a terminating radical which can be hydrogen, an alkyl group of one to six carbon atoms, an ester group such as acyl, or an aryl group such as phenyl; m has a value of two to eight; p and s have values such that the oxyalkylene segment —$(C_2H_4O)_p$—$(C_3H_6O)_s$— has a molecular weight in the range of 200 to 5,000; the segment preferably having fifty to one hundred mole percent of oxyethylene units —$(C_2H_4O)_p$— and one to fifty mole percent of oxypropylene units —$(C_3H_6O)_s$—; x has a value of 8 to 400; and y has a value of 2 to 40. Preferably each of $R^{10}$, $R^{11}$, $R^{12}$ and $R^{13}$ is a methyl group; $R^c$ is H; m is preferably three or four whereby the group $R^b$ is most preferably the radical —$(CH_2)_3$—; and the values of p and s are such as to provide a molecular weight of the oxyalkylene segment —$(C_2H_4O)_p$—$(C_3H_6O)_s$— of between about 1,000 to 3,000. Most preferably p and s should each have a value of about 18 to 28.

A second siloxane polyether (copolyol) has the Formula II:

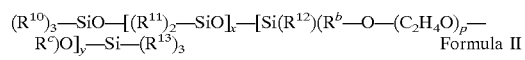

$(R^{10})_3$—SiO—[$(R^{11})_2$—SiO]$_x$—[Si($R^{12}$)($R^b$—O—$(C_2H_4O)_p$—$R^c$)O]$_y$—Si—$(R^{13})_3$    Formula II wherein p has a value of 6 to 16; x has a value of 6 to 100; and y has a value of 1 to 20 and the other moieties have the same definition as defined in Formula I.

It should be understood that in both Formulas I and II shown above, that the siloxane-oxyalkylene copolymers of the present invention may, in alternate embodiments, take the form of endblocked polyethers in which the linking group $R^b$, the oxyalkylene segments, and the terminating radical $R^c$ occupy positions bonded to the ends of the siloxane chain, rather than being bonded to a silicon atom in the siloxane chain. Thus, one or more of the $R^{10}$, $R^{11}$, $R^{12}$ and $R^{13}$ substituents which are attached to the two terminal silicon atoms at the end of the siloxane chain can be substituted with the segment —$R^b$—O—$(C_2H_4O)_p$—$(C_3H_6O)_s$—$R^c$ or with the segment —$R^b$—O—$(C_2H_4O)_p$—$R^c$. In some instances, it may be desirable to provide the segment —$R^b$—O—$(C_2H_4O)_p$—$(C_3H_6O)_s$—$R^c$ or the segment —$R^b$—O—$(C_2H_4O)_p$—$R^c$ at locations which are in the siloxane chain as well as at locations at one or both of the siloxane chain ends.

Particular examples of suitable dimethicone copolyols are available either commercially or experimentally from a variety of suppliers including Dow Corning Corporation, Midland, Mich.; General Electric Company, Waterford, N.Y.; and Witco Corp., Greenwich, Conn. Examples of specific products include DOW CORNING® 5225C from Dow Corning; SILWET L-7622 from Witco; and various dimethicone copolyols available either commercially or experimentally from GE, such as SF 1528. It should also be noted that various concentrations of the dimethicone copolyols in cyclomethicone can be used. While a concentration of 10% in cyclomethicone is frequently seen commercially, other concentrations can be made by stripping off the cyclomethicone or adding additional cyclomethicone.

For the silicone phase examples of the non-ionic emulsifier having an HLB value less than 7 include:

(a) ethoxylated alcohols such as steareth-2, nonoxynol-2, PPG-4-Ceteth-1;

(b) ethoxylated carboxylic acids such as PEG-4 dilaurate, PEG-2 oleate;

(c) glyceryl esters such as PEG-2 castor oil, polyglyceryl-3 oleate, glyceryl stearate;

(d) sorbitan derivatives such as sorbitan oleate.

For the silicone phase, examples of non-volatile silicones (that is, silicones with a boiling point above 250 degrees C at atmospheric pressure) include phenyl trimethicone, dimethicone, phenylpropyltrimethicone (SF1555 from General Electric, Waterford, N.Y.), cetyl dimethicone, and dimethiconol as well as two or more of the forgoing.

For the silicone phase, examples of volatile silicones (that is, silicones with a boiling point of 250 degrees C or less at atmospheric pressure) include cyclomethicone (especially cyclopentasiloxane, also called "D5"), "hexamethyldisiloxane", and low viscosity dimethicone (for example, Dow Corning® 200 fluid having a viscosity of 1–2 centistokes).

It should be noted that organic emollients can be substituted for all or a portion of the non-volatile silicones. While the organic emollients can also be substituted for a portion of the volatile silicones, this is less desirable.

The compositions of the present invention can include other optional ingredients to improve the aesthetics and/or performance of the cosmetic compositions of the invention. These include colorants, fillers, fragrances, emollients, masking agents, etc.

Emollients are a known class of materials in this art, imparting a soothing effect to the skin. These are ingredients which help to maintain the soft, smooth, and pliable appearance of the skin. Emollients are also known to reduce whitening on the skin and/or improve aesthetics. Examples of chemical classes from which suitable emollients can be found include:

(a) fats and oils which are the glyceryl esters of fatty acids, or triglycerides, normally found in animal and plant tissues, including those which have been hydrogenated to reduce or eliminate unsaturation. Also included are synthetically prepared esters of glycerin and fatty acids. Isolated and purified fatty acids can be esterified with glycerin to yield mono-, di-, and triglycerides. These are relatively pure fats which differ only slightly from the fats and oils found in nature. The general structure may be represented by Formula VI:

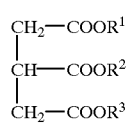

Formula VI wherein each of $R^1$, $R^2$, and $R^3$ may be the same or different and have a carbon chain length (saturated or unsaturated) of 7 to 30. Specific examples include peanut oil, sesame oil, avocado oil, coconut, cocoa butter, almond oil, safflower oil, corn oil, cotton seed oil, castor oil, hydrogenated castor oil, olive oil, jojoba oil, cod liver oil, palm oil, soybean oil, wheat germ oil, linseed oil, and sunflower seed oil.

(b) hydrocarbons which are a group of compounds containing only carbon and hydrogen. These are derived from petrochemicals. Their structures can vary widely and include aliphatic, alicyclic and aromatic compounds. Specific examples include paraffin, petrolatum, hydrogenated polyisobutene, and mineral oil.

(c) esters which chemically, are the covalent compounds formed between acids and alcohols. Esters can be formed from almost all acids (carboxylic and inorganic) and any alcohol. Esters here are derived from carboxylic acids and an alcohol. The general structure would be $R^4CO$—$OR^5$. The total number of carbons for $R^4$ and $R^5$ together can vary from 7 to 50 (particularly 14–30) and can be saturated or unsaturated, straight chained or branched. Specific examples include isopropyl myristate, isopropyl palmitate, isopropyl stearate, isopropyl isostearate, butyl stearate, octyl stearate, hexyl laurate, cetyl stearate, diisopropyl adipate, isodecyl oleate, diisopropyl sebacate, isostearyl lactate, $C_{12-15}$ alkyl benzoates, myreth-3 myristate, dioctyl malate, neopentyl glycol diheptanoate, dipropylene glycol dibenzoate, $C_{12-15}$ alcohols lactate, isohexyl decanoate, isohexyl caprate, diethylene glycol dioctanoate, octyl isononanoate, isodecyl octanoate, diethylene glycol diisononanoate, isononyl isononanoate, isostearyl isostearate, behenyl behenate, $C_{12-15}$ alkyl fumarate, laureth-2 benzoate, propylene glycol isoceteth-3 acetate, propylene glycol ceteth-3 acetate, octyldodecyl myristate, cetyl ricinoleate, myristyl myristate.

(d) saturated and unsaturated fatty alcohols (primary, secondary and tertiary alcohols, and including guerbet alcohols) with general structure:

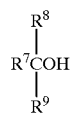

wherein each of $R^7$, $R^8$ and $R^9$ is hydrogen or a straight or branched chain carbon group and the total number of carbons in $R^7+R^8+R^9$ is in the range of 7–30. Specific examples include lauryl, myristyl, cetyl, isocetyl, stearyl, isostearyl, oleyl, ricinoleyl and erucyl alcohol.

(e) lanolin and its derivatives which are a complex esterified mixture of high molecular weight esters of (hydroxylated) fatty acids with aliphatic and alicyclic alcohols and sterols as well as propoxylated and/or butoxylated species. Specific examples include lanolin, lanolin oil, lanolin wax, lanolin alcohols, lanolin fatty acids, isopropyl lanolate, propoxylated lanolin, butoxylated lanolin, and acetylated lanolin alcohols.

(f) alkoxylated alcohols wherein the alcohol portion is selected from aliphatic alcohols having 2–18 and more particularly 4–18 carbons, and the alkylene oxide portion is selected from the group consisting of propylene oxide and butylene oxide having a number of alkylene oxide units from 2–53 and, more particularly, from 2–15. Specific examples include PPG-14 butyl ether and PPG-53 butyl ether.

(g) mixtures and blends of two or more of the foregoing.

Particular examples of emollients for the silicone phase include organic emollients selected from:

(a) propoxylated alcohols such as PPG-3 myristyl ether and PPG-14 butyl ether;

(b) propoxylated acids such as PPG-2 isostearate, PPG-4jojoba acid;

(c) fats and oils such as avocado oil and mink oil;

(d) hydrocarbons such as mineral oil and squalane;

(e) lanolin and lanolin derivatives such as lanolin, lanolin oil;

(f) fatty esters such as isopropyl myristate, C12–15 alkyl benzoate, dioctyl adipate, and octylmethoxycinnamate;

The emollient or emollient mixture or blend thereof incorporated in compositions according to the present invention can, illustratively, be included in amounts of 0–25%, particularly 1–25%, particularly 3–20% and, even more particularly, 8–15% by weight, based on the total weight of the composition.

Optionally other ingredients can be added to the silicone phase. Such ingredients include viscosity enhancing agents (for example, linear and branched high molecular weight silicone gums and elastomers and organic polymers) and a gelling agent selected from the group consisting of amide siloxane polymer (for example, the polyamide gelling agents described in copending cases U.S. Ser. Nos. 08/790,351 filed on Jan. 24, 1997 (and earlier provisional cases referenced therein); and 08/904,709, filed on August 1, 1997, all of which are incorporated by reference in their entirety herein), for example, Example 2 of U.S. Ser. No. 08/904,709 listed above. A deodorant fragrance may be used in an amount of 0.05–5.0% by weight based on the total weight of the composition.

An important part of the invention is the processing of the combined ingredients. The same formulation will exhibit different rheological properties depending on how the formulation is processed. The formulation will become thicker as the processing energy is increased until a point is reached where too much energy is supplied and the emulsion is broken. The energy is usually supplied to the formulation in the form of mechanical energy via a homogenizer, but other sources of energy can be used such as heat energy or sonic energy. The components of the silicone phase are blended until uniform. In a separate kettle, the components of the active phase are blended until uniform. Preferably the two blending steps are done at room temperature, but elevated temperatures can be used such as in the range of 50–95 degrees C. The active phase is then added slowly with adequate agitation to the silicone phase to form an emulsion. The emulsion is then homogenized to improve the quality of the emulsion and increase the viscosity of the emulsion. However, overprocessing of the emulsion can result in breaking the emulsion resulting in a loss of viscosity and separation of the phases.

It should be noted that the viscosity of the compositions is usually controlled by the processing conditions as previously described. While it is not a requirement that a thickening agent be included, it may be convenient, for example, for time or energy or formulation reasons to use such a thickening agent rather than alter the processing conditions.

Advantageously the formulations of this invention can be used in selected applicators to achieve improved aesthetics. For example, the formulations of this invention can be used in an applicator with a mesh fabric applicator surface (for example, a woven fabric surface, a non-woven fabric surface, an apertured extruded film such as is described in a recently filed copending cases U.S. Ser. No. 09/168,144, filed Oct. 7, 1998, and U.S. Ser. No. 09/233,807, filed Nov. 4, 1998, and incorporated herein by reference in their entireties, owned by the same entity as this application) to obtain a drier feel when the formulation is applied to the underarm area. It is also possible to use the formulations of this inventions in an aerosol applicator which also has some type of mesh structure as the applicator surface. Examples of such applicators have been listed above.

Various combinations of applicators and formulations may be selected. One method of accomplishing this improved and/or drier feel is to use formulations of this invention with a viscosity of 60,000–150,000, particularly with a viscosity of 80,000–120,000 in an applicator having a porous surface as is described in copending cases IR 6020 and 6020-01 referenced herein. For such an applicator, a pore size of 50–300 microns, especially 80–120 microns is advantageous. In another example, compositions of this invention having a viscosity in the range of 2000–30,000 may be used with aerosol applicators having a porous surface such as are described in U.S. Pat. No. 5,813,785, listed above. Yet another type of applicator useful with the formulations of this invention is a sintered porous applicator. Examples of these types of porous applicators may be found in PCT case WO 98/04236 assigned to The Gillette Company; WO 98/12122 assigned to the Procter & Gamble Company; and EP 775 641 A1.

A particular set of embodiments of the invention are antiperspirant and/or deodorant cosmetic products comprising a composition in an applicator having a porous applicator surface wherein the applicator is selected from the group consisting of:

(a) an applicator comprising (i) a container which defines a reservoir for the composition, (ii) an applicator head having pores with an average diameter of 50–300 microns which are interconnected with each other in all directions, which head is affixed at one end of said container to form a porous applicator surface, and (iii) a means for compressing the composition to force the composition from the reservoir through the pores;

(b) an applicator having a barrel with an elevator adapted to move axially within the barrel, and closed at another end by a porous applicator surface, said porous applicator surface comprised of at least one of a woven and a non-woven fabric, said fabric bonded to an insert frame, the fabric having apertures of 50–300 microns, the composition flowing through the porous applicator surface with substantially no post-extrusion flow; and (c) an applicator for a composition which is a liquid to be applied to a surface comprising (i) a container for the liquid, the container being a pressurized reservoir equipped with a dispenser valve; (ii) a head operatively connected to the container wherein the head is made of a porous material which is a sintered body having a porosity in the range of 50–300 microns to form a porous applicator surface; and (iii) a cap for operatively connecting the head to the container.

In particular, the formulations of this invention are able to be applied to give a drier feel and better aesthetics while minimizing the problems of leakage from the applicators.

In a preferred embodiment of the invention a clear emulsion may be obtained. This is done by selecting the types and amounts of materials so that the refractive indices of the silicone phase and the active phase are as close as possible.

In another embodiment, up to 10% (for example 5–10%) of water can be added to an anhydrous formulation without a deleterious effect.

In general, applicators useful in combination with the compositions described above may be described as having the following components:

(a) a container which defines a reservoir for holding a selected quantity of the composition (for example, a plastic structure of any convenient shape);

(b) an applicator surface particularly located in a head structure which head structure is affixed to the container and which has pores 50–300 microns in size; and (c) a transport means to force the composition up to and through and onto the applicator surface (for example, a deformable container which may be squeezed to force the composition out, a push up cyclinder which may be pushed upwardly to force the composition out, an advancing screw mechanism which may be turned to reduce the volume of the container and force the composition out, etc.).

The applicator surface may be selected from a variety of structures for example:

(a) a sintered plastic such as Porex material which has interconnected pores and which is formed from small plastic particles;

(b) a woven material (such as polyethylene or some other suitable plastic) which may be a single layer or multiple layers and which may be arranged to have straight pore alignment or off-set pore alignment;

(c) a non-woven material which may be a single layer or multiple layers and which (if used as multiple layers) may be arranged to have straight pore alignment or off-set pore alignment selected from the group consisting of:

(i) an extruded plastic film formed with or after treated to have pores;

(ii) a sheet structure formed with a plurality of strands; and (d) combinations of any of the foregoing; wherein each individual layer has pores 50–300 microns in size.

These types of applicators are more fully described in the IR6020 and IR 6020-01 copending applications referenced herein.

For one type of embodiment of the package useful in this invention, one or more plies of a mesh fabric with substantially linear openings through the fabric are used to form an applicator surface. The use of one ply or a plurality of plies will depend on a variety of factors such as the structure of the fabric, the fiber denier, the weave of the fabric, whether the fabric is woven or non-woven, the size of the apertures for an extruded non-woven film fabric, and the porosity of the fabric if it is a non-woven with randomly arrayed fibers. In one embodiment the fabric is heat bondable to a peripheral frame edge and the product in the package has a viscosity of 2,000–200,000 centipoise. A particular embodiment would include the use of a packaged product where the applicator surface was a single ply woven fabric of a denier and weave or a single ply of a non-woven layer (as described above) that can be used with or without an underlying support structure. This would allow for flexing of the surface to follow the contours of the skin without permanent distortion of the fabric surface. In another option a plurality of fabric plies can be used (for example 2–10 plies, preferably 2–5 plies). By randomly overlaying the plies of fabric, the openings are partially juxtaposed from ply layer to ply layer thereby creating a circuitous path of the product through the mesh fabric.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

Throughout the present specification, "antiperspirant active" and "deodorant active" materials are discussed. Both types of materials contribute to reduction of body malodor, for example, axillary malodor. By reduction of body malodor, it is meant that, generally, there is less body malodor after application of the composition to a person's skin, as compared to a person's malodor without application of the composition. Such reduction can be due to a masking of the malodor, absorption and/or chemical reaction of the malodorous material, reduction of the levels of the bacteria producing the malodorous materials, for example, from perspiration, reduction of perspiration, etc. The antiperspirant active materials, when utilized in appropriate amounts, primarily act to reduce malodor by reducing perspiration; the antiperspirant active materials can also have a deodorant function, for example, as an antimicrobial or bacteriostatic agent. The deodorant active materials do not substantially reduce perspiration, but reduce malodor in other ways. For example, as fragrances masking the malodor or reducing the malodor intensity; absorbents; antimicrobial (bacteriostatic) agents; or agents chemically reacting with malodorous materials.

EXAMPLES

The following Examples are offered as illustrative of the invention and are not to be construed as limitations thereon. In the Examples and elsewhere in the description of the invention, chemical symbols and terminology have their usual and customary meanings. In the Examples as elsewhere in this application values for n, m, etc. in formulas, molecular weights and degree of ethoxylation or propoxylation are averages. Temperatures are in degrees C unless otherwise indicated. As is true for the rest of the application as well, the amounts of the components are in weight percents based on the standard described; if no other standard is described then the total weight of the composition is to be inferred. Various names of chemical components include those listed in the *CTFA International Cosmetic Ingredient Dictionary* (Cosmetics, Toiletry and Fragrance Association, Inc., $7^{th}$ ed. 1997). Viscosities were measured using Brookfield viscometers unless otherwise indicated.

Example 1

An antiperspirant composition can be made as a 200 g sample. Dimethicone copolyol (10% in cyclomethicone) (8.0 g) is mixed with cyclomethicone (Dow Corning® DC 245) (52.0 g) at room temperature with stirring until the mixture is homogeneous. In a separate vessel at room temperature the following materials are combined and mixed until a clear and homogeneous mixture is obtained: aluminum zirconium tetrachlorohydrex glycine (30% in propylene glycol) (Westchlor® ZR 35B 30% PG Solution from Westwood Chemical Corp., Middletown, N.Y.) (60.8 g),); propylene glycol (58.7 g); anhydrous ethanol (SDA 40 200) (18.0 g); Polysorbate-80 (0.5 g); and fragrance (2.0 g). The second mixture is then slowly added to the first mixture over a time period of 10 minutes. The resulting opaque emulsion is then subjected to homogenization. Homogenization is done with an Ultra-Turrax T25 machine (Janke & Kunkel, Germany).

Example 2

The method of Example 1 is repeated but with the following amounts of materials: 4.00% dimethicone copolyol (10% in cyclomethicone); 15.90% phenylpropyltrimethicone (SF 1555 from General Electric); 10.10% cyclomethicone (Dow Corning® DC 245); 30.40% aluminum zirconium tetrachlorohydrex gly (Westchlor® ZR 35B 30% PG Solution); 29.35% propylene glycol; 9.00% anhydrous ethanol (SDA 40 200); 0.25% Polysorbate-80 (Tween® 80 from ICI, Wilmington, Del.); and 1.00% fragrance.

Example 3

A clear antiperspirant composition is made by combining dimethicone copolyol (10% in cyclomethicone) (40.52 g); C12–C15 alkyl benzoate (Finsolv® TN, from Finetex Inc., Elmwood Park, N.J.) (60.17 g); and cyclomethicone (Dow Corning® 245 Fluid) (49.83g) and mixing them at 500 rpm until the mixture is homogeneous to form Phase A. The refractive index is measured to be 1.4340. Phase B is made by combining an antiperspirant active (Westchlor® ZR 35B 30% PG Solution) (152.07 g); Polysorbate 80 (1.30 g); propylene glycol (146.82 g); ethanol (95% alcohol) (45.06 g); and fragrance (5.02 g) and mixing the ingredients of Phase B with a magnetic stirrer until homogeneous. The refractive index can be obtained as 1.4350. Phase B is added to Phase A over a period of 30 minutes with stirring at 500 rpm. Mixing is continued for an additional 30 minutes at 700 rpm. Homogenization is done for 2 minutes with a Gifford-Wood Model 1L homogenizer. The composition is allowed to sit overnight. Viscosity is obtained at 2.5 rpm/T bar E. Processing can be controlled so that the final viscosity after homogenization is 58,000 cps.

Example 4
Composition for Aerosol With Porous Structure

A composition suitable for use in an applicator such as is described in U.S. Pat. No. 5,567,073 can be made as follows. For a 500 gram batch Part A is made by combining phenyl trimethicone (Dow Corning® 556) (73.15 g, 14.63%); cyclomethicone (Dow Corning® 245) (46.85 g, 9.37%); amide-siloxane polymer as described in Example 2 of U.S. Ser. No. 08/904,709 listed above; (10.00 g, 2.00%); dimethicone copolyol (10% in cyclomethicone) (Dow Corning® 5225C) (5.00 g, 1.00%) in a first vessel and mixing the ingredients on a Lightnin® Mixer on moderate speed (about 300 rpm) with heat (about 110 degrees C) until the mixture is clear. The mixture is then cooled to about 50 degrees C. Part B is made by combining propylene glycol (169.55 g, 33.91%); aluminum zirconium tetrachlorohydrex GLY (Westchlor® ZR 35B 30% PG Solution) (150.00 g, 30.00%); anhydrous ethanol (SDA 40, 200 proof) (39.45 g, 7.89%); Polysorbate 20 (Tween® 20 from ICI) (1.00 g, 0.20%); and fragrance (5.00 g, 1.00%). The ingredients for Part B are mixed in a separate vessel equipped with a magnetic stirring bar mixer. After Part B is mixed, it is gradually added to Part A in the first vessel over a period of 15 minutes with mixing using a Lightnin® Mixer at about 500 rpm. The combined mixture is mixed for an additional 15 minutes with an increase in speed to 700 rpm. The set-up is switched to a homogenizer and the mixture is homogenized for 1 minute. The viscosity before homogenization is determined with a RV #4 Spindle at 4 rpm as 6500. After 24 hours the viscosity is measured as being 11,000.

Example 5

An antiperspirant gel suitable for use in a microscreen applicator can be made as follows. Part A is made by combining dimethicone copolyol (10% in cyclomethicone) (Dow Corning® 5225-C) (100.00 g, 20.00%); and phenyl-trimethicone (Dow Corning® 556) (105.00 g, 21.00%) in a vessel with mixing. Part B is made by combining fragrance (5.00 g, 1.00%); antiperspirant active (Westchlor® ZR 35B 30% PG Solution) (152.00 g, 30.40%); propylene glycol (78.00 g, 15.60%); Polysorbate 20 (5.00 g, 1.00%); and anhydrous ethanol (55.00 g, 11.00%) with mixing. Part B is added to Part A using a mixing speed of 500–700 rpm. The composition is further homogenized for 2 minutes with a Gifford-Wood Model 1L homogenizer. The viscosity is measured with a T bar C at 2.5 rpm as 33,000.

Example 6

The method of Example 5 was repeated except with the following amounts of ingredients: Part A: dimethicone copolyol (10% in cyclomethicone) (25.45 g, 5.09%); phenyltrimethicone (65.50 g, 13.10%) and, as an additional ingredient, cyclomethicone (57.55 g, 11.51%). For Part B: fragrance (5.00 g, 1.00%); antiperspirant active as described above (152.00 g, 30.40%); propylene glycol (147.40 g, 29.48%); Polysorbate 20 (1.50 g, 0.30%); and anhydrous ethanol (45.60 g, 9.12%). The viscosity as measured by T bar E at 2.5 rpm is 48,000.

Example 7

A 1600 g batch of an antiperspirant composition can be made as follows. Part A is made by combining phenyl dimethicone (SF 1550, General Electric) (235.04 g); cyclomethicone and dimethicone copolyol (same type as in Example 1) (240.16 g) in a first vessel and mixing the ingredients with a Lightnin® Mixer on moderate speed (about 500 rpm). Part B can be made by combining propylene glycol (472.80 g); antiperspirant active (Westchlor ZR 35B 30% PG Solution) (486.40 g); anhydrous ethanol (145.92 g); Polysorbate 80 (Tween® 80 NF, from ICI) (3.68 g); and fragrance (16.00 g) in a second vessel equipped with a magnetic stirring bar mixer. After (Part B is mixed, it is gradually added to Part A in the first vessel over a period of 15 minutes using a Lightnin® Mixer at about 500 rpm. The total mixture is mixed for an additional 15 minutes and the speed is increased to 700 rpm. The apparatus is then switched to a Gifford-Wood Model 1L homogenizer and homogenized for 1 minute. A composition with a viscosity of 120,000 may be obtained (as measured with a T bar E at 2.5 rpm).

Example 8

The method described in Example 7 can be repeated except that 352.80 g (22.05%) of propylene glycol and 120.00 g (7.509%) water are used in place of the 472.80 g of propylene glycol in Example 7. A composition with a viscosity of 120,000 may be obtained (as measured with a T bar E at 2.5 rpm).

Examples 9 The method of Example 7 can be repeated with the following amounts of ingredients: Part A: dimethicone copolyol (Dow Corning® 5225 C) (500 g, 10%); phenyl trimethicone (Dow Corning® 556) (955 g, 19.1%); cyclomethicone (Dow Corning® 245) (195 g, 3.9%). Part B: antiperspirant active (aluminum zirconium tetrachlorohydrex gly (REACH 908 PG 30%) (1570 g, 31.4%); propylene glycol (1180 g, 23.6%); anhydrous ethanol (500 g, 10%); Polysorbate-20 (50 g, 1%); and fragrance (50 g, 1%). Homogenization is continued for 20 minutes on a Gifford-Wood Model 1L homogenizer. A composition with a viscosity of 74,000 can be obtained as measured with a T bar E at 2.5 rpm.

Example 9A
Leakage Test

Seventy five grams of an antiperspirant product ma de according to Example 9 but without homogenization so as to have a viscosity of 4,000 cps when measured with a T bar E at 2.5 rpm were placed in a commercial gel package (Speed Stick® Gel) and in a package suitable for use with this invention (sintered plastic applicator with pore size of 100 microns). Both packages were inverted for a period of 25 seconds at which time the product had almost completely leaked out of the gel package (at a rate of about 134 g/min). The package with the composition of the invention lost product at the significantly slower rate of 0.05 grams per minute.

Example 10

The formulation of Example 9 was made with a viscosity of 74,000 (as measured with a T bar E at 2.5 rpm) and evaluated for the effect of the applicator on dry feel. The formulation by itself and the formulation/package combination were each evaluated by a panel of trained evaluators. In one case the product was applied to the axilla from the back of a spoon, in the other case a similar amount of the product was applied from a package equipped with a porous sintered applicator (100 micron) of the invention. The package used w as generally of the type described in EP 0 732 273 B1 with a convex oval dome having a major axis of 5.0 cm and a minor axis of 2.5 cm. The dome was attached to a container with a capacity of about 85 g and the product was extruded using a dial mechanism. The following table shows that the trained evaluators found the product delivered from the package equipped with the porous applicator significantly (95% confidence level) drier for the duration of the 30 minute evaluation period. The scale used was 0=wet, 8=dry.

| FEELS DRY IN THE AXILLA | | | | | | | | |
|---|---|---|---|---|---|---|---|---|
| Time in minutes | 1 | 3 | 5 | 10 | 15 | 20 | 25 | 30 |
| Dryness rating with porous applicator | 2.2 | 3.7 | 5.1 | 6.0 | 6.5 | 7.0 | 7.3 | 7.6 |
| Dryness rating without applicator | 1.2 | 2.5 | 3.9 | 4.9 | 5.7 | 6.5 | 6.8 | 7.3 |

Example 11

The formulation of Example 10 was evaluated for dry feel by a panel of 9 human subjects. In one case the product was applied from a commercial clear antiperspirant package (Speed Stick® Gel) and in the other the product was applied from the sintered porous applicator described in Example 10. The panelists said the product applied from the porous package was drier. On a scale where 1 is "not wet" and 7 is "wet" the panelists rated the product from the gel package 5.1 and the product from the porous package 4.1. This difference is significant at the 85% confidence level.

We claim:

1. A liquid composition which is made by combining an active phase and a silicone phase wherein:
   (a) the active phase is made by combining:
      (i) 10–70% of a glycol selected from the group consisting of propylene glycol, dipropylene glycol, tripropylene glycol, 2-methyl-1,3-propanediol, low molecular weight polyethylene glycol, and mixtures of any of the foregoing;
      (ii) 0.1–10% of a nonionic emulsifier having an HLB greater than 8;
      (iii) 0.01–30% (on an anhydrous solids basis) of a cosmetically active ingredient selected from the group consisting of antiperspirant actives and deodorant actives which cosmetically active ingredient is in the form of a powder or a solution; and
      (iv) 0–20% of an alcohol selected from the group consisting of ethanol and isopropanol, aqueous solutions thereof and mixtures of any of the foregoing;
   (b) the silicone phase is made by combining:
      (i) from 0.1–10% of an emulsifier selected from the group consisting of
         (1) at least one dimethicone copolyol having an HLB less than 7;
         (2) at least one nonionic emulsifier having an HLB value less than 7; and
         (3) mixtures of (1) and (2);
      (ii) 0–30% of a non-volatile silicone;
      (iii) 0–30% of a volatile silicone; and
      (iv) 0–25% of an organic emollient; provided that:
   (a) the silicone phase contains at least 10% silicone;
   (b) that the ratio of silicone phase to active phase is in the range of 1:1 to 1:4;
   (c) the composition is processed to maintain a viscosity in the range of 2,000–200,000 centipoise; and
   (d) the composition contains no more than 10% water.

2. A composition according to claim 1 in which the alcohol is added in an amount of 5–20%.

3. A composition according to claim 1 in which for the active phase the nonionic emulsifier having an HLB greater than 8 comprises at least one member selected from the group consisting of:
   (a) sorbitan esters and ethoxylated sorbitan esters;
   (b) ethoxylates suitable for cosmetic use;
   (c) PEG esters;
   (d) propoxylates suitable for cosmetic use;
   (e) ethoxylated modified triglycerides;
   (f) alkylphenol aromatic ethoxylates;
   (g) block copolymers which are alkoxylated glycols having ethoxylated and propoxylated segments; and
   (h) silicone polyethers.

4. A composition according to claim 3 in which the nonionic emulsifier having an HLB greater than 8 is selected from the group consisting of:
   (a) sorbitan esters and ethoxylated sorbitan esters selected from the group consisting of PEG-20 sorbitan isostearate, sorbitan monolaurate, polysorbate-20, polysorbate-40, polysorbate-60, and polysorbate-80;
   (b) ethoxylates selected from the group consisting of Ceteth-20, PEG-30 castor oil, PEG-40 hydrogenated castor oil, PEG-60 hydrogenated castor oil, Laureth-7, Isolaureth-6, Steareth-10, Steareth-20, Steareth-2 1, Steareth-100, Ceteareth-1 2, Oleth-5, and Oleth-10;
   (c) PEG esters selected from the group consisting of PEG-8 oleate, PEG-8 laurate, PEG-8 dilaurate, PEG-12 dilaurate, PEG-80 diisostearate, PEG-25 stearate, PEG-40 stearate, and PEG-100 stearate;
   (d) propoxylates selected from the group consisting of PPG-2-ceteareth-9, and PPG-5-ceteth-20;
   (e) ethoxylated modified triglycerides selected from the group consisting of PEG-20 corn glycerides, and PEG-12 palm kernel glycerides;
   (f) alkylphenol aromatic ethoxylates selected from the group consisting octoxynol-20 and nonoxynol-40;
   (g) block copolymers which are alkoxylated glycols having ethoxylated and propoxylated segments and which are selected from the group consisting of Poloxamer 124 and Poloxamer 234; and
   (h) silicone polyethers which are dimethicone copolyols.

5. A composition according to claim 1 wherein the cosmetically active ingredient is an antiperspirant active material selected from the group consisting of aluminum chlorides; zirconyl hydroxychlorides; zirconyl oxychlorides; basic aluminum chlorides; basic aluminum chlorides combined with at least one of zirconyl oxychlorides and hydroxychlorides; and organic complexes of each of basic aluminum chlorides with or without zirconyl oxychlorides and hydroxychlorides and mixtures of any of the foregoing.

6. A composition according to claim 5 wherein the cosmetically active ingredient is an antiperspirant active material selected from the group consisting of aluminum chlorohydrate, aluminum chloride, aluminum sesquichlorohydrate, aluminum chlorohydrol-propylene glycol complex; zirconyl hydroxychloride, aluminum-zirconium glycine complex, aluminum chlorohydrex PG, aluminum chlorohydrex PEG, aluminum dichlorohydrex PG, aluminum dichlorohydrate, aluminum dichlorohydrex PEG, aluminum zirconium trichlorohydrex gly propylene glycol complex, aluminum zirconium trichlorohydrex gly dipropylene glycol complex, aluminum zirconium tetrachlorohydrex gly propylene glycol complex, aluminum zirconium tetrachlorohydrex gly dipropylene glycol complex, and mixtures of any of the foregoing.

7. A composition according to claim 1 wherein the cosmetically active ingredient is a deodorant active selected from the group consisting of deodorizing amounts of:

(a) fragrances;

(b) antimicrobial agents; and (c) antiperspirant agents.

8. A composition according to claim 1 wherein the dimethicone copolyols having an HLB less than 7 are selected from the group consisting of compounds of:

(a) a first siloxane polyether of Formula I:

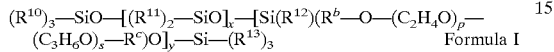  Formula I wherein each of $R^{10}$, $R^{11}$, $R^{12}$ and $R^{13}$ may be the same or different and each is selected from the group consisting of C1–C6 alkyl; $R^b$ is the radical —$C_mH_{2m}$—; $R^c$ is a terminating radical which can be hydrogen, an alkyl group of one to six carbon atoms, an ester group or an aryl group; m has a value of two to eight; p and s have values such that the oxyalkylene segment —$(C_2H_4O)_p$—$(C_3H_6O)_s$— has a molecular weight in the range of 200 to 5,000; and (b) a second siloxane polyether of Formula II:

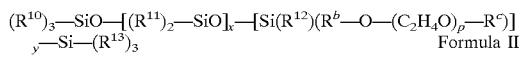  Formula II wherein p has a value of 6 to 16; x has a value of 6 to 100; and y has a value of 1 to 20 and the other moieties have the same definition as defined in Formula I.

9. A composition according to claim 1 wherein the nonionic emulsifier having an HLB less than 7 is selected from the group consisting of:

(a) ethoxylated alcohols;

(b) ethoxylated carboxylic acids;

(c) glyceryl esters; and (d) sorbitan derivatives.

10. A composition according to claim 9 wherein the nonionic emulsifier having an HLB less than 7 is selected from the group consisting of:

(a) ethoxylated alcohols selected from the group consisting of steareth-2, nonoxynol-2, and PPG-4-Ceteth-1;

(b) ethoxylated carboxylic acids selected from the group consisting of PEG-4 dilaurate, and PEG-2 oleate;

(c) glyceryl esters selected from the group consisting of PEG-2 castor oil, polyglyceryl-3 oleate, and glyceryl stearate; and (d) sorbitan oleate.

11. A composition according to claim 1 wherein the non-volatile silicone has a boiling point above 250 degrees C at atmospheric pressure and is selected from the group consisting of phenyl trimethicone, dimethicone, and phenylpropyltrimethicone.

12. A composition according to claim 1 wherein the volatile silicone has a boiling point of 250 degrees C or less at atmospheric pressure and is selected from the group consisting of cyclomethicones and low viscosity dimethicones.

13. A composition according to claim 1 to which is additionally added an emollient.

14. A composition according to claim 13 in which the emollient is selected from the group consisting of:

(a) fats and oils which are selected from the group consisting of:

(i) the glyceryl esters of fatty acids, or triglycerides, normally found in animal and plant tissues, including those which have been hydrogenated to reduce or eliminate unsaturation;

(ii) synthetically prepared esters of glycerin and fatty acids;

(iii) isolated and purified fatty acids esterified with glycerin to yield mono-, di-, and triglycerides;

(b) hydrocarbons which are selected from the group consisting of aliphatic, alicyclic and aromatic compounds;

(c) esters of formula $R^4CO$—$OR^5$ wherein the total number of carbons for $R^4$ and $R^5$ together is in the range of 7 to 50 and wherein each of $R^4$ and $R^5$ can be saturated or unsaturated, straight chained or branched;

(d) primary, secondary and tertiary saturated and unsaturated fatty alcohols having a general structure:

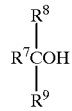

wherein each of $R^7$, $R^8$ and $R^9$ is hydrogen or a straight or branched chain carbon group and the total number of carbons in $R^7+R^8+R^9$ is in the range of 7–30;

(e) lanolin and its derivatives which are selected from the group consisting of lanolin, lanolin oil, lanolin wax, lanolin alcohols, lanolin fatty acids, isopropyl lanolate, propoxylated lanolin, butoxylated lanolin, and acetylated lanolin alcohols;

(f) alkoxylated alcohols wherein the alcohol portion is selected from aliphatic alcohols having 2–18 and the alkylene oxide portion is selected from the group consisting of propylene oxide and butylene oxide having a number of alkylene oxide units from 2–53; and (g) mixtures and blends of two or more of the foregoing.

15. An antiperspirant and/or deodorant cosmetic product comprising a composition of any one of claims 1 or 3–15 in an applicator having a porous applicator surface wherein the applicator is comprised of:

(a) a container which defines a reservoir for holding a selected quantity of the composition;

(b) an applicator surface located in a head structure which head structure is affixed to the container and which has a plurality of pores 50–300 microns in size; and (c) a transport means to force the composition up to, through and onto the applicator surface.

16. An antiperspirant and/or deodorant cosmetic product comprising a composition of any one of claims 1 or 3–14 in an applicator having a porous applicator surface wherein the applicator is comprised of:

(a) a container which defines a reservoir for holding a selected quantity of the composition;

(b) an applicator surface particularly located in a head structure which head structure is affixed to the container and which has a plurality of pores; and (c) a transport means to force the composition up to and through and onto the applicator surface; and wherein the applicator surface is selected from the group consisting of:

(a) a sintered plastic which has interconnected pores and which is formed from small plastic particles;

(b) a woven material which may be a single layer or multiple layers and which may be arranged to have straight pore alignment or off-set pore alignment;

(c) a non-woven material which may be a single layer or multiple layers and which, if used as multiple layers, may be arranged to have straight pore alignment or off-set pore alignment wherein the non-woven material is selected from the group consisting of:
   (i) an extruded plastic film formed with or after treated to have pores;
   (ii) a sheet structure formed with a plurality of strands; and
(d) combinations of any of the foregoing; wherein each individual layer has pores 50–300 microns in size.

17. An antiperspirant and/or deodorant cosmetic product comprising a composition of any one of claims 1 or 3–14 in an applicator having a porous applicator surface wherein the applicator is selected from the group consisting of:
   (a) an applicator comprising (i) a container which defines a reservoir for the composition of any one of claims 1 or 3–14, (ii) an applicator head having pores with an average diameter of 50–300 microns which are interconnected with each other in all directions, which head is affixed at one end of said container to form a porous applicator surface, and (iii) a means for compressing the composition to force the composition from the reservoir through the pores;
   (b) an applicator having a barrel with an elevator adapted to move axially within said barrel, and closed at another end by a porous applicator surface, said porous applicator surface comprised of at least one of a woven and a non-woven fabric, said fabric bonded to an insert frame, said fabric having apertures of 50–300 microns, said composition flowing through said porous applicator surface with substantially no post-extrusion flow; and
   (c) an applicator for a composition of any one of claims 1 or 3–14 which is a liquid to be applied to a surface comprising (i) a container for the liquid, the container being a pressurized reservoir equipped with a dispenser valve; (ii) a head operatively connected to the container wherein the head is made of a porous material which is a sintered body having a porosity in the range of 50–300 microns to form a porous applicator surface; and (iii) a cap for operatively connecting the head to the container.

18. A composition according to any one of claims 1 or 3–14 which is anhydrous.

* * * * *